United States Patent
Menon et al.

(10) Patent No.: US 6,792,357 B2
(45) Date of Patent: Sep. 14, 2004

(54) OPTICAL CORROSION MEASUREMENT SYSTEM

(75) Inventors: Sunil Menon, Golden Valley, MN (US); Lewis P. Olson, Apple Valley, MN (US); Russell Braunling, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/229,797

(22) Filed: Aug. 27, 2002

(65) Prior Publication Data

US 2004/0044483 A1 Mar. 4, 2004

(51) Int. Cl.[7] .............................................. G01N 31/00
(52) U.S. Cl. ........................... 702/27; 702/28; 702/34; 702/35; 356/237.2; 422/53
(58) Field of Search ........................... 73/623; 422/53, 422/55, 14, 15, 18; 702/27, 28, 29, 32, 33, 34, 35, 36, 51, 155, 156; 356/237.2, 300; 250/341.1, 301

(56) References Cited

U.S. PATENT DOCUMENTS

| | | | |
|---|---|---|---|
| 4,403,294 A | | 9/1983 | Hamada et al. |
| 4,597,294 A | * | 7/1986 | Brill et al. ................ 73/623 |
| 5,155,555 A | | 10/1992 | Wetgrove et al. |
| 5,208,162 A | | 5/1993 | Osborne et al. |
| 5,332,900 A | | 7/1994 | Witzke et al. |
| 5,376,331 A | * | 12/1994 | Bucher et al. ............ 422/18 |
| 5,623,341 A | | 4/1997 | Hunt |
| 5,682,102 A | * | 10/1997 | Takahashi et al. ........ 324/545 |

FOREIGN PATENT DOCUMENTS

| | | |
|---|---|---|
| DE | 4139107 | 7/1993 |
| DE | 10102387 | 5/2002 |
| JP | 07005117 | 10/1995 |

\* cited by examiner

*Primary Examiner*—Bryan Bui
(74) *Attorney, Agent, or Firm*—Kris T. Fredrick

(57) ABSTRACT

A system for measuring pitting corrosion in metal using a digital camera having a lens and an output unit for identifying the color of a metal coupon on a gray scale and providing an output in the midrange of the scale when non corroded and different output after exposure to a corrosive environment. A computer is connected to the output of the camera to display the photographs to permit observation of the gray scale output based upon a minimum and maximum threshold inputs which are adjustable based on an observation of pitting. The points of interest on the coupon representing observed pitting are recorded and summed to calculate an estimated corrosion area corresponding to pitting the said coupon as a percentage of the total coupon area.

21 Claims, 2 Drawing Sheets

OPTICAL CORROSION MEASUREMENT SYSTEM

FIELD OF THE INVENTION

The present invention relates to a system for optically measuring pitting and general corrosion in surfaces of metals. More particularly the invention relates to an optical system for measuring more than one type of corrosion in metals such as aluminum.

BACKGROUND OF THE INVENTION

At the present time, corrosion-related experiments are performed on metal coupons in order to obtain information about the use of the metal in actual applications. Metal coupons are the "work-horse" of the corrosion monitoring industry, and it is a very cheap method for what is now a multi-million dollar industry. The coupons are examined for corrosion after exposure to predetermined and measured conditions using several methods.

One method is based on weight-loss of the coupons. The coupon weight before and after the corrosion experiment provides a difference that is related to corrosion activity. Another method is to measure changes in electrical resistance, but this requires sophisticated calibrations that are difficult to interpret. Visual inspection of the coupon is also performed to determine the area of the coupon that is affected by corrosion. Both these corrosion measurements are inaccurate and subjective.

Other methods have been proposed for observing materials. U.S. Pat. No. 5,332,900, Witzke et al. uses an on-line monitoring system in which the metal is irradiated and observed with an optical system. U.S. Pat. No. 5,623,341, Hunt, uses nonlinear second order surface spectroscopy to monitor the condition of a surface for corrosion and other changes. U.S. Pat. No. 5,208,162, Osborne et al., employs a piezoelectric crystal system. U.S. Pat. No. 5,155,555 uses a coupon that is inserted into a fluid and removed for observation using reflected light. None of these systems provide for a simple and effective method for measurement of corrosion on metal such as metal coupons.

It would be of great advantage in the art if a more accurate method of measuring corrosion activity could be provided.

It would be another great advance in the art if the method of measuring corrosion activity would reduce or eliminate subjective measurements, and quantify actual corrosion activity.

Another advantage would be if calculations of the corrosion activity could be done autonomously.

Other advantages will appear hereinafter.

SUMMARY OF THE INVENTION

It has now been discovered that the above and other objects of the present invention may be accomplished in the following manner. Specifically, the present invention provides a process for autonomously determining the amount of corrosion that has occurred to a metal coupon, such as an aluminum coupon, for a given environment and time. The invention comprises a combination of a digital camera focused on a metal coupon, providing digital images of the coupon by the digital camera, and analyzing the image using an algorithm.

The Coupons that are used are cropped within the field of view of a macro lens digital camera. The digitization consists of intensity values of from 0 to 255, with 0 representing the color black and 255 representing the color white. Inbetween 0 and 255 are varying shades of gray. An image of a non-corroded coupon, or calibration coupon, is taken to get the minimum and maximum intensity values. The intensity values that trend toward 0 or black are an indication of corrosion by pitting. Intensity values that trend toward 255 or white are an indication of oxidization.

Using the corrosion image from the digital camera, a threshold for the image is calculated and the values that are greater than or less than that of the threshold are summed, to give an estimated area of corrosion for the coupon. Varying the threshold and observing the resulting image with the original corrosion image gives a better estimate of the corrosion for the coupon being inspected. Black pixels indicate a pitting action, so changing the threshold for black pixels will isolate the pits and cumulative pit area can be estimated by summing the pixels that are less than a given threshold.

The pixels are arranged using a standard clustering algorithm such as the k-means algorithm. Then, the type of corrosion, pitting or general, is determined using a classification algorithm such as one using neural networks.

BRIEF DESCRIPTION OF THE DRAWINGS

For a more complete understanding of the invention, reference is hereby made to the drawings, in which.

DETAILED DESCRIPTION OF THE PREFERRED EMBODIMENT

The present invention has been used to measure corrosion of metals such as aluminum in various environments and over varying periods of time in order to evaluate the potential risk of using such metals over periods of time in actual applications.

Figure 1:
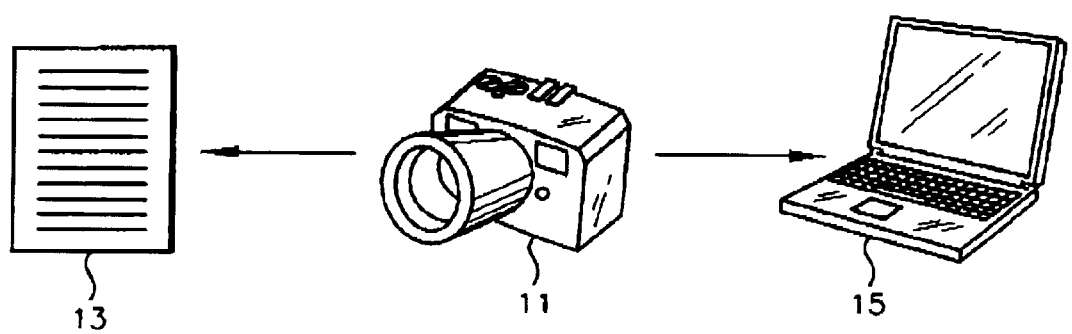
FIG. 1 a schematic diagram of the physical components of the present invention.

As shown in FIG. 1, a digital camera 11 is focused on a metal coupon 13 and the resulting image in digital form is transmitted to image analysis software in a computer 15. By knowing the size of coupon 13, and using a camera lens slightly larger than coupon 13, the camera 11 is then adjusted to crop the image detected to the actual coupon size to eliminate all background images.

Figure 2:
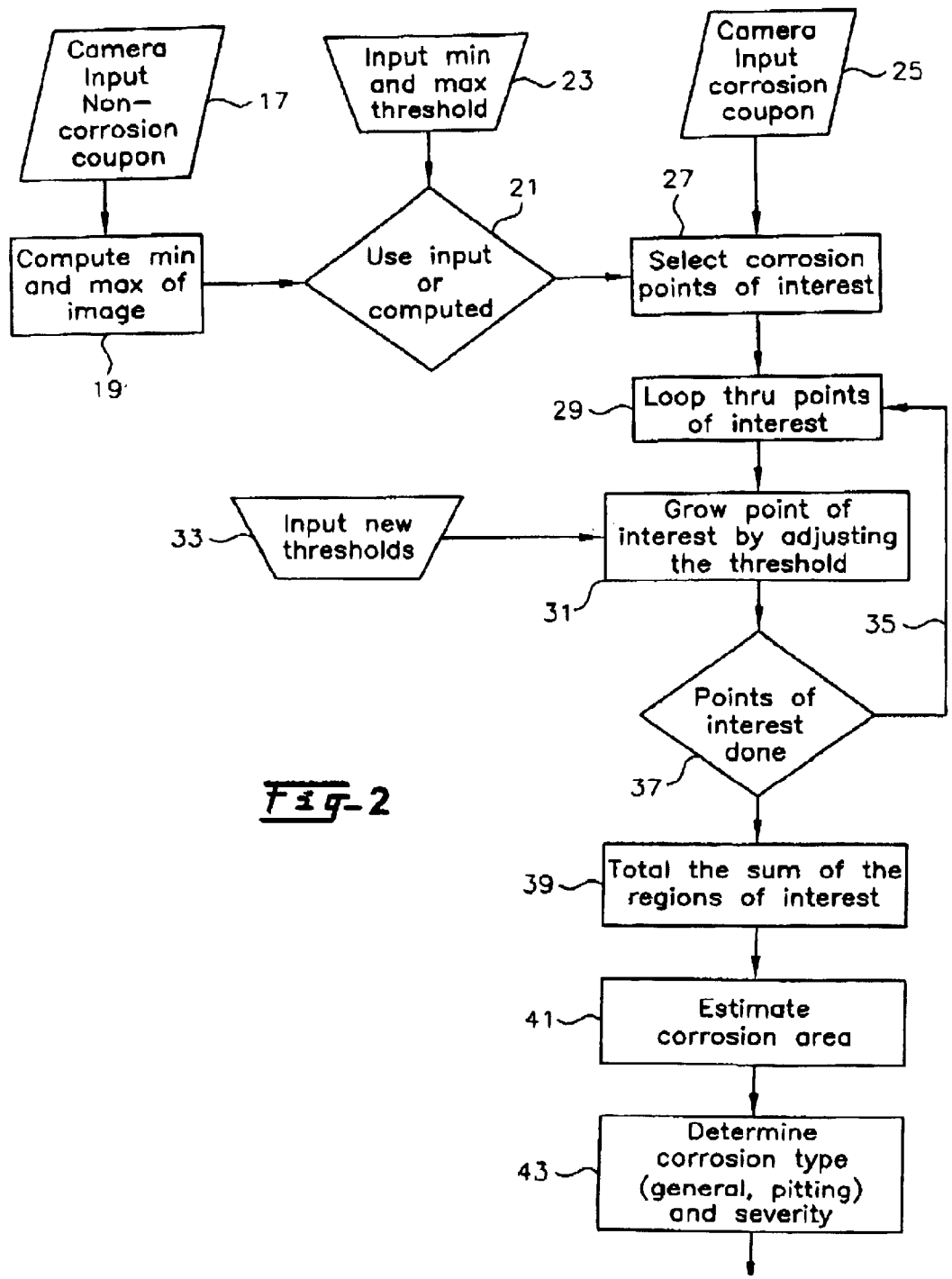
FIG. 2 is a schematic flow diagram illustrating the method of the invention.

In FIG. 2, the camera is first focused on a non-corroded coupon in box 17 to produce a signal that is processed by the computer to give a scale of color in box 19 from a minimum to the maximum of the image received. The computer gets the data in box 21 to recognize the minimum and maximum using this input from the computations in box 19. Alternatively, known or predetermined minimum and maximum thresholds from box 23 may be used.

As noted above, the gray scale 0–255 is the standard gray scale (from black to white) for eight bit processing. An actual coupon is photographed under set lighting conditions, whereby the light is adjusted to avoid readings near 0 or 255, and the environmental testing is begun. Additional digital photographs are taken at points during the time of the test. A typical non corroded coupon has a reading of from about 140 to about 180 for the camera and lighting used for evaluating the present invention. However, with different cameras and different lighting, other base thresholds are measured.

Other data from the camera provides information on other phenomena. For example: 200–255 is nearly white and represents oxidation; 140–180 represents an non corroded coupon; and 70–120 represents staining and is not really corrosion. 0–70 represents pitting.

Once one has focused on the area that is corroded, the type of corrosion can be determined based on the distribution of corroded spots on the area. Pitting is single points of degradation on a surface area, and the present invention distinguishes between oxidation and general corrosion which is equally distributed over the surface. The distance between pits is measured to help with making these distinctions of types of corrosion.

The initial threshold, say for example 140, is used as the lowest value maximum threshold for the untested coupon. This number is inputted as data, so the display shows the initial photo and the test photo at a given time. When the initial threshold is inputted, the threshold will show some gray other than pitting, and the coupon is inspected, visually by a technician or via a software scan, to input new thresholds so that the only area shown is with a readout of actual pitting, between 0 and 70. The computer then calculates the percent actual pitting based on the total area of the coupon.

The camera 11 is then focused on a coupon 13 in a controlled environment and adjusted to give selected corrosion points of interest from box 25. Because corrosion leading to pitting is not uniform on a metal surface, the most severe points of corrosion are selected, as in box 27. At specific intervals of time, the data is also transmitted to a summing box 29 and then as data to memory 31 where the threshold is adjusted via new threshold inputs from box 33 to produce a set of data for each period of time. This data is looped back via line 35 from box 37, to summing box 29 during each interval of time and added to the memory box 31. Box 37 functions as a data accumulator and/or switch to send data either back via line 35 to summing box 29 or, when the test is completed, or when the predetermined time for the specific test is complete, the data is transmitted to a compiling box 39, which totals the sum of the regions of interest. Data transmitted to estimating box 41 compares the area of corrosion measured to the total coupon area, which becomes a measured value that can be used to estimate the rate of corrosion of the metal. A visual or printout final determination is supplied by output box 43.

The space corroded as a percent of total space is calculated and an estimated rate of corrosion is calculated by determining what area is changing and what area has new regions of corrosion activity. Changing numbers give the rate of corrosion.

In order to determine if the corrosion is pitting or general, a clustering algorithm is used to determine how the areas of corrosion activity are distributed. If the areas of corrosion activity are very closely distributed, the clustering algorithm associates these areas to be part of the same cluster. Areas of corrosion activity that are spatially separated are associated, by the clustering algorithm, with different clusters. Once the clusters have been identified, a classification algorithm, such as using neural networks, is used to determine if the corrosion activity clusters, as determined by the clustering algorithm, indicate pitting or general corrosion. The corrosion activity calculation, followed by the clustering and classification steps, enables the invention to run autonomously.

The k-means algorithm is a method of clustering data points into k disjoint subsets such that the sum of squares of the difference of the data points and the centroids of each of the subsets is minimized. The k-means algorithm and clustering algorithms used in this invention are available in Metlab®, a commercial software package. Classification is the process of associating the clusters identified above with specific attributes such as corrosion type (general and pitting). In this invention, the specific classification algorithms are also in Metlab®. Metlab® software is made by a company called The Mathworks, located in Natick, Mass.

In use the invention includes photographs (using the digital camera as explained) every week for a period of time, such as four to six weeks, to watch the growth of pits, using different temperatures and relative humidity. Some environments take up to one year to show significant corrosion and others only take one week. By varying the conditions of the environment with a series of tests at measured environments, trends with respect to the conditions are developed that predict the effect incurred in relatively benign conditions without having to wait for the year or more for real-time data.

The invention has been used to quantify corrosion in an aircraft, by performing experiments in simulations of conditions and tracking the time. The old way was to measure the pit size mechanically, but this invention permits it to be autonomously quantified. The results are used in evaluating aircraft condition. A substantial amount of the work has been done with aluminum, but other metals that both pit and oxidize can be evaluated. Pitting type corrosion is of primary interest for this invention and metal oxidation is incidental.

While particular embodiments of the present invention have been illustrated and described, it is not intended to limit the invention, except as defined by the following claims.

What is claimed is:

1. A system for measuring pitting corrosion in metal, comprising:
    a digital camera having a lens and an output unit for identifying the color of a metal coupon on a gray scale and providing an output in the midrange of the scale;
    a coupon aligned to be photographed by said camera in a non corroded state, said coupon being positioned to provide a gray scale reading in the midrange to produce a first photograph and to be photographed at least one additional time after being exposed to a corrosion environment;
    a computer connected to receive the output of said camera output and having a display for comparative display of said first photograph and said at least one additional time to permit observation of the gray scale output thereof, said computer being adapted to adjust the output display based upon a minimum and maximum threshold input and exclude output outside said threshold, said minimum and maximum threshold inputs being adjustable based on an observation of pitting;
    a recorder for recording the points of interest on said coupon representing observed pitting, said recorder being adapted to sum the regions of interest, said computer being adapted to calculate an estimated corrosion area corresponding to pitting on said coupon as a percentage of the total coupon area.

2. The system of claim 1, wherein said gray scale is 0 to 255 pixel gray scale.

3. The system of claim 2, wherein the midrange of said gray scale output ranges from 140 to 180 and said coupon is aluminum.

4. The system of claim 1, wherein an initial minimum threshold is visually distinguishable from complete black on the scale and the maximum threshold is the lowest gray scale reading of said non corroded coupon.

5. The system of claim 4, wherein the initial minimum threshold is from about 10 to about 20 and the maximum threshold is about 140, both based on a scale of 0 (black) to 255 (white).

6. The system of claim 1, wherein the coupon is aluminum and is photographed a plurality of times after being exposed to a corrosion environment to provide a time and corrosion relationship.

7. The system of claim 1, which further includes a clustering algorithm in said computer.

8. A system for measuring pitting corrosion in metal, comprising:

digital camera means having a lens and an output unit for identifying the color of a metal coupon on a gray scale and providing an output in the midrange of the scale;

a coupon aligned to be photographed by said camera in a non corroded state, said coupon being positioned to provide a gray scale reading in the midrange to produce a first photograph and to be photographed at least one additional time after being exposed to a corrosion environment;

computer means connected to receive the output of said camera output and having a display for comparative display of said first photograph and said at least one additional time to permit observation of the gray scale output thereof, said computer means being adapted to adjust the output display based upon a minimum and maximum threshold input and exclude output outside said threshold, said minimum and maximum threshold inputs being adjustable based on an observation of pitting;

recorder means for recording the points of interest on said coupon representing observed pitting, said recorder means being adapted to sum the regions of interest, said computer means being adapted to calculate an estimated corrosion area corresponding to pitting on said coupon as a percentage of the total coupon area.

9. The system of claim 8, wherein said gray scale is 0 to 255 pixel gray scale.

10. The system of claim 9, wherein the midrange of said gray scale output ranges from 140 to 180 and said coupon is aluminum.

11. The system of claim 8, wherein an initial minimum threshold is visually distinguishable from complete black on the scale and the maximum threshold is the lowest gray scale reading of said non corroded coupon.

12. The system of claim 11, wherein the initial minimum threshold is from about 10 to about 20 and the maximum threshold is about 140, both based on a scale of 0 (black) to 255 (white).

13. The system of claim 8, wherein the coupon is aluminum and is photographed a plurality of times after being exposed to a corrosion environment to provide a time and corrosion relationship.

14. A method for measuring pitting corrosion in metal, comprising:

focusing a digital camera having a lens and an output unit on a metal coupon;

photographing said coupon in a non corroded state, said coupon being positioned to provide a gray scale reading in the midrange to produce a first photograph and photographing said coupon at least one additional time after being exposed to a corrosion environment;

providing output from said camera output unit for displaying a comparative display of said first photograph and said at least one additional time to permit observation of the gray scale output thereof;

adjusting the output display based upon a minimum and maximum threshold input and excluding output outside said threshold;

adjusting said minimum and maximum threshold inputs based on an observation of pitting;

recording the points of interest on said coupon representing observed pitting; and summing the regions of interest and calculating an estimated corrosion area corresponding to pitting on said coupon as a percentage of the total coupon area.

15. The method of claim 14, wherein said gray scale is 0 to 255 pixel gray scale.

16. The method of claim 15, wherein the midrange of said gray scale output ranges from 140 to 180.

17. The method of claim 14, wherein an initial minimum threshold is visually distinguishable from complete black on the scale and the maximum threshold is the lowest gray scale reading of said non corroded coupon.

18. The method of claim 17, wherein the initial minimum threshold is from about 10 to about 20 and the maximum threshold is about 140, both based on a scale of 0 (black) to 255 (white).

19. The method of claim 14, wherein the coupon is aluminum and is photographed a plurality of times after being exposed to a corrosion environment to provide a time and corrosion relationship.

20. A method for measuring pitting corrosion in metal, comprising:

focusing a digital camera having a lens and an output unit on a metal coupon;

photographing said coupon in a non corroded state, said coupon being positioned to provide a 0 to 255 pixel gray scale reading in the midrange thereof ranging from 140 to 180 to produce a first photograph and photographing said coupon at least one additional time after being exposed to a corrosion environment;

providing output from said camera output unit for displaying a comparative display of said first photograph and said at least one additional time to permit observation of the gray scale output thereof;

adjusting the output display based upon a minimum and maximum threshold input visually distinguishable from complete black on the scale and a maximum threshold using the lowest gray scale reading of said non corroded coupon and excluding output outside said threshold;

adjusting said minimum and maximum threshold inputs based on an observation of pitting;

recording the points of interest on said coupon representing observed pitting; and summing the regions of interest and calculating an estimated corrosion area corresponding to pitting on said coupon as a percentage of the total coupon area.

21. The method of claim 20, wherein the coupon is photographed a plurality of times after being exposed to a corrosion environment to provide a time and corrosion relationship.

* * * * *